United States Patent

Hirai et al.

Patent Number: 5,128,366
Date of Patent: Jul. 7, 1992

[54] PYRROLE DERIVATIVES

[75] Inventors: Kentaro Hirai, Kyoto; Teruyuki Ishiba, Osaka; Haruo Koike, Kyoto; Masamichi Watanabe, Shiga, all of Japan

[73] Assignee: Shinogi & Co., Ltd., Osaka, Japan

[21] Appl. No.: 707,805

[22] Filed: May 30, 1991

[30] Foreign Application Priority Data

Jul. 5, 1990 [JP] Japan .................. 2-178564

[51] Int. Cl.$^5$ .................. A61K 31/40; C07D 215/36; C07D 207/48; C07D 409/02
[52] U.S. Cl. .................. 514/422; 514/424; 514/314; 546/172; 548/517; 548/527; 548/542
[58] Field of Search .................. 548/527, 517, 542; 514/422, 424, 314; 546/172

[56] References Cited

U.S. PATENT DOCUMENTS 4,885,307 12/1989 Toja et al. .................. 548/542

FOREIGN PATENT DOCUMENTS

| 287890 | 10/1988 | European Pat. Off. | 548/542 |
| 300249 | 1/1989 | European Pat. Off. | 548/542 |
| 330172 | 8/1989 | European Pat. Off. | 548/542 |
| 8702662 | 5/1987 | PCT Int'l Appl. | 548/542 |

Primary Examiner—Mary C. Lee
Assistant Examiner—Joseph K. McKane
Attorney, Agent, or Firm—Wenderoth, Lind & Ponack

[57] ABSTRACT

The compounds of the present invention inhibit HMG-CoA reductase, and subsequently suppress the synthesis of cholesterol. And they are useful in the treatment of hypercholesterolemia, hyperlipoproteinemia, and atherosclerosis. The compounds have the formula

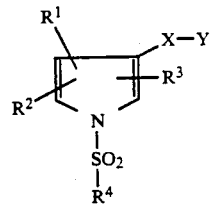

wherein $R^1$, $R^2$, and $R^3$ each is independently hydrogen, optionally substituted lower alkyl, or optionally substituted aryl; $R^4$ is lower alkyl, aralkyl, aryl, or heteroaryl, each of which is optionally substituted; X is vinylene or ethylene; Y is

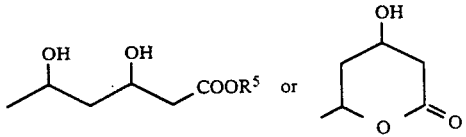

where $R^5$ is hydrogen, lower alkyl, aryl, aralkyl, or a cation capable of forming a non-toxic pharmaceutically acceptable salt.

8 Claims, No Drawings

PYRROLE DERIVATIVES

BACKGROUND OF THE INVENTION

1. Field of the Invention

The present invention relates to 3-hydroxy-3-methyl-glutaryl coenzyme A (HMG-CoA) reductase inhibitor.

2. Prior Art

As the first generation of drugs for the treatment of atherosclerosis by inhibiting the activity of HMG-CoA reductase, there are known Mevinolin (U.S. Pat. No. 4,321,938), pravastatin (JP Unexamed. Pat. Publn. No. 59-48418), and simvastatin (U.S. Pat. No. 4,444,784,), which are fungal metabolites or of the chemical modifications. Recently, synthetic inhibitors of HMG-CoA reductase such as fluvastatin (F. G. Kathawala et al, 8th Int'l Symp. on Atherosclerosis, Abstract Papers, p. 445, Rome (1988)) and BMY 22089 (GB Pat. No. 2,202,846) are developed as the second generation drugs (Pharmacia, the science of the drug, vol. 26, No. 5 p. 453–454, 1990)).

SUMMARY OF THE INVENTION

The present invention relates to 3-hydroxy-3-methyl-glutaryl coenzyme A (HMG-CoA) reductase inhibitor. The compounds of this invention inhibit the HMG-CoA reductase, which plays a main role in the synthesis of cholesterol, and subsequently they suppress the synthesis of cholesterol. Therefore, they are useful in the treatment of hypercholesterolemia, hyperlipoproteinemia, and atherosclerosis.

DETAILED DESCRIPTION

The present invention relates to compounds of the formula:

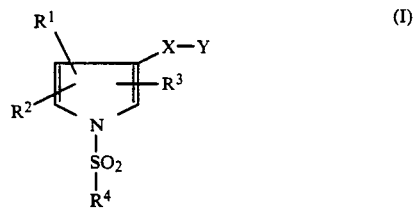

wherein $R^1$, $R^2$, and $R^3$ each is independently hydrogen, optionally substituted lower alkyl, or optionally substituted aryl; $R^4$ is lower alkyl, aralkyl, aryl, or heteroaryl, each of which is optionally substituted; X is vinylene or ethylene; Y is

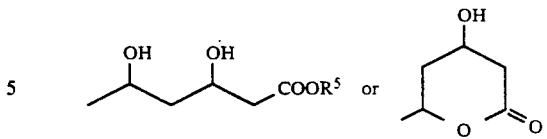

where $R^5$ is hydrogen, lower alkyl, aryl, aralkyl, or a cation capable of forming a non-toxic pharmaceutically acceptable salt.

In the specification, the term "lower alkyl" refers to a straight or branched chain $C_1$ to $C_6$ alkyl, including methyl, ethyl, n-propyl, isopropyl, n-butyl, isobutyl, sec-butyl, tert-butyl, n-pentyl, isopentyl, neopentyl, tert-pentyl, 2-methylbutyl, n-hexyl, isohexyl and the like. Further, the lower alkyl may be substituted by 1 to 3 substituents independently selected from the group consisting of halogen, lower alkoxyamino and cyano.

The term "aryl" refers to $C_6$ to $C_{12}$ aromatic group including phenyl, tolyl, xylyl, biphenylyl, naphthyl, and the like. The aryl may have 1 to 3 substituents independently selected from the group consisting of lower alkyl, halogen, amino, and cyano. Preferred aryls are phenyl, biphenylyl, or naphthyl having 1 to 3 substituents selected from the group consisting of lower alkyl and halogen.

The term "aralkyl" means the above-mentioned alkyl substituted by the above-mentioned aryl at an optional position. Examples of them are benzyl, phenethyl, phenylpropyl and the like. The aralkyl may have 1 to 3 substituents independently selected from the group consisting of lower alkyl, halogen, amino, cyano, and the like.

The term "heteroaryl" refers to 5- or 6-membered heterocyclic group containing 1 or 2 atoms selected from the group consisting of oxygen, sulfur, and nitrogen, and may be condensed with 5- or 6-membered aromatic group. Examples of them are thienyl, furyl, pyrrolyl, imidazolyl, pyrazolyl, isothiazolyl, pyridyl, pyrimidinyl, pyrazinyl, quinolyl, isoquinolyl, benzothienyl, indolyl, and the like, preferably thienyl, quinolyl, and benzothienyl. Further the group may have 1 to 3 substituents selected from the group consisting of lower alkyl, halogen, amino and cyano.

The term "halogen" refers to fluorine, chlorine, bromine, and iodine.

The term "a cation capable of forming a non-toxic pharmaceutically acceptable salt" refers to alkali metal ion, alkaline earth metal ion, and ammonium ion. Examples of alkali metal are lithium, sodium, potassium, and cesium, and examples of alkaline earth metal are beryllium, magnesium, and calcium, preferably sodium and potassium.

The compounds of the present invention can be prepared by the following method.

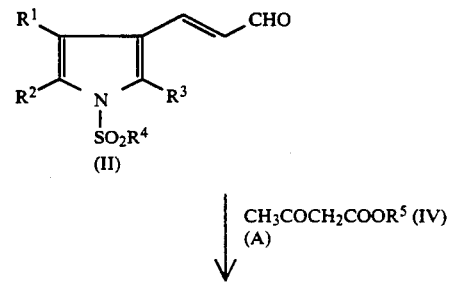

-continued

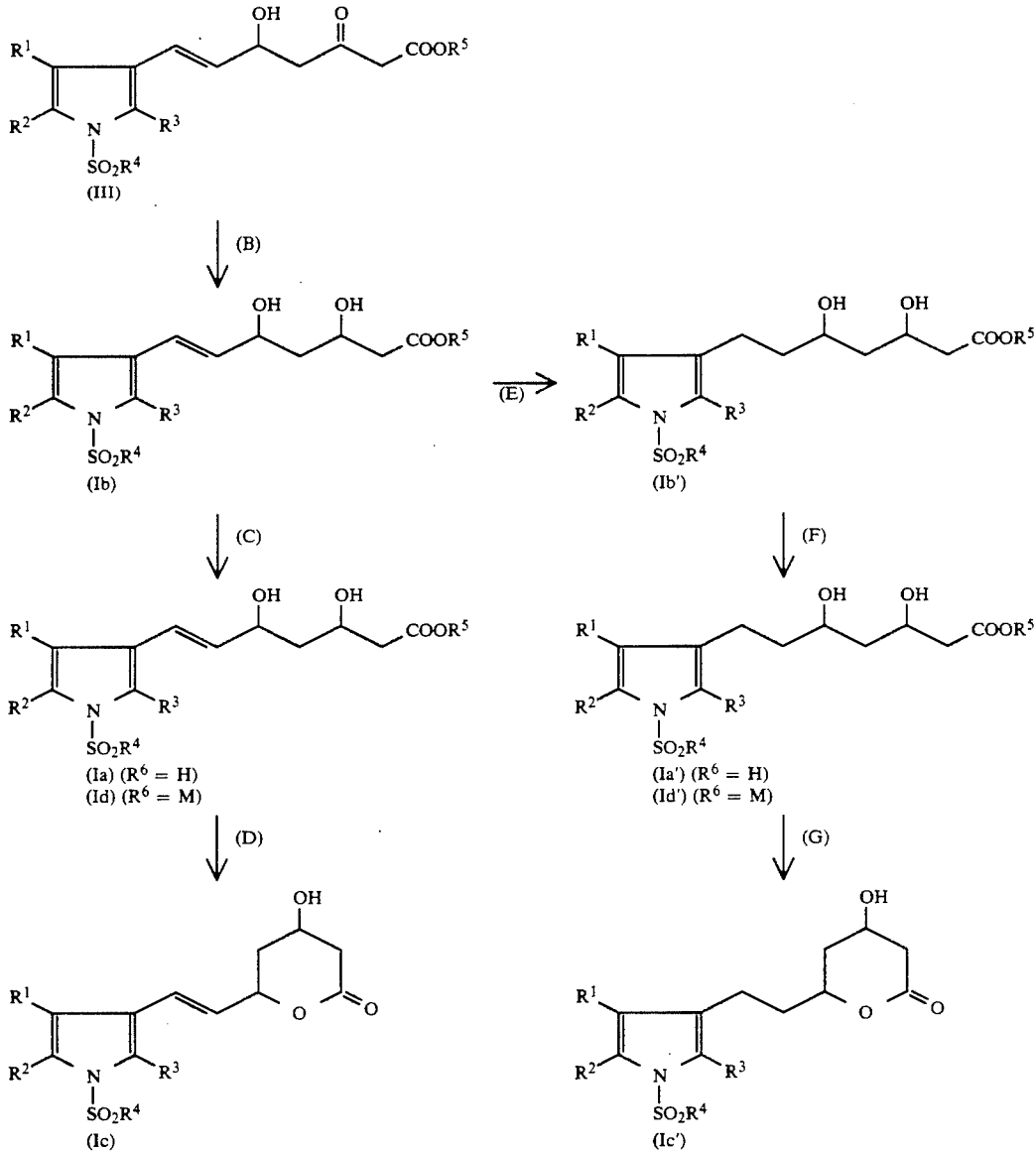

(Wherein M means metallic ion or ammonium ion).

STEP A

The compound (II) in an organic solvent is added dropwise to a dianion organic solution, which is prepared from sodium hydride and butyllithium, of the compound (IV), if necessary under nitrogen atmosphere to give the compound (III).

The reaction is performed preferably under cooling at −80° to 0° C., for 10 minutes to 10 hours, preferably 30 minutes to 3 hours.

Organic solvents which may be used are ethers such as diethylether and tetrahydrofuran, dimethylformamide, acetonitrile, and the like, most preferably tetrahydrofuran.

STEP B

The compound (III) is treated with diethylmethoxyborane and $NaBH_4$ in alcoholic organic solvent under cooling, then the reaction mixture is chromatographed on silica gel to give the compound (Ib).

The reaction is performed under cooling at −80° to 0° C., for 5 minutes to 5 hours, preferably for 30 minutes to 2 hours.

Alcohols which may be used are methanol, ethanol, propanol, butanol, and the like.

The same organic solvents as in STEP A may be used.

STEP C

The compound (I b) is hydrolyzed, then neutralized with acid, and extracted with an organic solvent to give the compound (I a). Alternatively, after the hydrolysis, the reaction mixture is evaporated under reduced pressure and freeze-dried to give the compound (Id).

The hydrolysis is performed by an ordinary method in solvents such as water, alcohols, dioxane, acetone, or their mixture, preferably in the presence of a base.

The reaction temperature is 0° to 50° C., preferably at or near room temperature.

The base may be sodium hydroxide, potassium hydroxide, or their analogue.

The acids mean inorganic acids such as hydrochloric acid, sulfuric acid, and the like.

STEP D

The compound (Ia) or (Id) is refluxed in an organic solvent, if necessary under heating to give the compound (Ic).

The reaction is performed for 1 to 10 hours, preferably for 3 to 5 hours, under heating.

Organic solvents which may be used are the same solvent as in Step A, or benzene, toluene, dichlorethane, and the like.

The compound (Ic) is alternatively prepared by leaving the compound (Ia) or (Id) standing at room temperature for 50 to 100 days. However this procedure needs a long term, usually the former procedure is adopted.

STEP E

The compound (Ib') is prepared by the reduction of the compound (Ib).

The reaction is performed in an appropriate inactive solvent in the presence of the catalyst for the catalytic reduction at 10° to 50° C., preferably at or near room temperature, for 30 minutes to 10 hours, preferably 5 to 7 hours.

Inactive solvents which may be used are water, acetic acid, methanol, ethanol, dioxane, and the like.

The catalysts which may be used are platinum-carbon, palladium-carbon, radium-carbon, and the like, most preferably palladium-carbon.

STEP F

The compound (Ib') is reacted in the same manner as in Step C to give the compound (Ia') or (Id').

STEP G

The compound (Ia') or (Id') is reacted in the same manner as in Step D to give the compound (Ic').

The compound of the present invention can be administered orally or parenterally. For example, the compound of the present invention may be orally administered in the form of tablets, powders, capsules, and granules, aqueous or oily suspension, or liquid form such as syrup or elixir, and parenterally in the form of injection of aqueous or oily suspension.

These preparation can be prepared in a conventional manner by using excipients, binders, lubricants, aqueous or oily solubilizers. emulsifier, suspending agents, and the like. Further, preservatives and stabilizers can be used.

The dosages may vary with the administration route and age, weight, conditions, and the kind of disease of the patients, but usually are 0.05-500 mg/day, preferably 0.5-200 mg/day through oral route, and 0.01-200 mg/day, preferably 0.1-100 mg/day through parenteral route in a single or divided doses.

The present invention is illustrated by the following examples and reference examples, which are not to be considered as limiting.

The abbreviations used in the examples and reference examples have the following meanings.

Me:methyl,
Et:ethyl,
i-Pr:isopropyl,
Ph:phenyl,
DMF:dimethylformamide,
Bz:benzyl
THF:tetrahydrofuran,
TFA:trifluoroacetic acid

EXAMPLE 1

(1) Ethyl 4-(4-fluorophenyl)-2-isopropylpyrrole-3-carboxylate 1

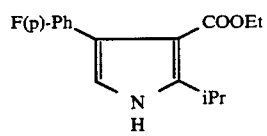

A mixture of 6.85 g (43.3 mmol) of ethyl isobutyrylacetate, 10.69 g (56.3 mmol) of 2-amino-4'-fluoracetophenone hydrochloride, 16.3 ml of acetic acid, 6.04 g of sodium acetate, and 10.8 ml of water is refluxed for 4 hours. After cooling, the reaction mixture is adjusted to pH 8 with saturated $NaHCO_3$ and extracted with ether. The extract, 8.36 g, is subjected to column chromatography with silica gel, eluting with methylene chloride to give 6.12 g (Yield:51.3%) of the compound 1.

NMR ($CDCl_3$) δ: 1.14 (t, 3H, J=7 Hz); 1.31 (d, 6H, J=7 Hz); 3.81 (septet, 1H, J=7 Hz); 4.15 (q, 2H, J=7 Hz); 6.58 (d, 1H, J=2,4 Hz); 6.96-7.05 (m, 2H); 7.29-7.37 (m, 2H); 8.36 (brs, 1H).

(2) Ethyl 4-(4-fluorophenyl)-2-isopropyl-1-phenylsulfonylpyrrole-3-carboxylate 2

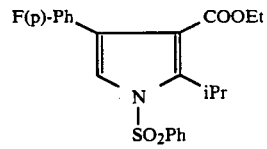

To a suspension of 948 mg (23.7 mmol) of 60% NaH in 50 ml of anhydrous DMF is added dropwise a solution of 5.93 g (21.5 mmol) of the compound 1 in 60 ml of anhydrous DMF under nitrogen atmosphere, and the reaction mixture is stirred for 30 minutes under ice-cooling. To the mixture is added dropwise a solution of 4.18 g (23.7 mmol) of benzene-sulfonyl chloride in 10 ml of anhydrous DMF, and the mixture is stirred at room temperature for 2 hours and with ice-water. The solution is extracted with ether, and the organic layer is washed with water to give 9.65 g of oil. It is subjected to column chromatography with silica gel, eluting with n-hexane/methylene chloride (1 /2) to give 8.65 g (Yield:96.6%) of the compound 2.

NMR ($CDCl_3$) δ: 1.10 (t, 3H, J=7 Hz); 1.14 (d, 6H, J=7 Hz); 3.57 (septet, 1H, J=7 Hz); 4.13 (q, 2H, J=7 Hz); 7.00-7.10 (m, 2H); 7.26-7.33 (m, 2H); 7.35 (s, 1H); 7.52-7.71 (m, 3H); 7.82-7.86 (m, 2H).

(3)
4-(4-Fluorophenyl)-3-hydroxymethyl-2-isopropyl-1-phenyl-sulfonylpyrrole 3

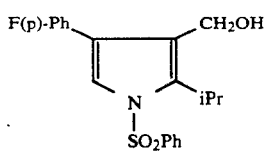

To a solution of 4.16 g (10 mmol) of the compound 2 in 200 ml of anhydrous toluene is added dropwise 25 ml of 1M . DIBAL in toluene under nitrogen atmosphere at −65° to −70° C. for 15 minutes, and the reaction mixture is stirred at the same temperature for 1 hour. To the reaction mixture are added water and 10% hydrochloric acid, the mixture is warmed up to room temperature and extracted with ether. The insoluble material is filtered off on celite. The ether layer is washed with water, dried and concentrated under reduced pressure to give 4.03 g (Yield:107.6%, containing the solvent) of the compound 3.

NMR (CDCl$_3$) δ: 1.17 (d, 6H, J=7 Hz); 3.61 (septet, 1H, J=7 Hz); 4.53 (d, 2H, J=4.7 Hz); 7.05–7.15 (m, 2H); 7.41 (s, 1H); 7.50–7.68 (m, 5H); 7.79–7.84 (m, 2H).

(4)
4-(4-Fluorophenyl)-3-formyl-2-isopropyl-1-phenylsulfonylpyrrole 4

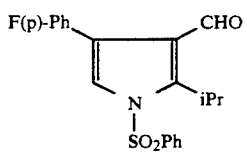

A mixture of 4.03 g (10.8 mmol) of the compound 3. 4.36 g (32.4 mmol) of N-methylmorpholine-N-oxide, 81 mg (0.23 mmol) of tetrapropylammonium perruthenate (TPAP), 20 g of powdered molecular sieves 4A, and 150 ml of methylene chloride is stirred at room temperature for 2 hours, and the insoluble material is filtered off on celite. The filtrate is concentrated to one-fifth of its original volume under reduced pressure. It is subjected to column chromatography with silica gel, eluting with methylene chloride to give 3.67 g (Yield: 91.2%) of the compound 4.

NMR (CDCl$_3$) δ: 1.16 (d, 6H, J=7 Hz); 3.715 (septet, 1H, J=7 Hz); 7.05–7.14 (m, 2H); 7.34–7.41 (m, 3H); 7.56–7.71 (m, 3H); 7.96–7.90 (m, 2H); 10.01 (s, 1H).

(5)
β-[4-(4-fluorophenyl)-2-isopropylpyrrol-3-yl]-(E)-acrylonitrile 5

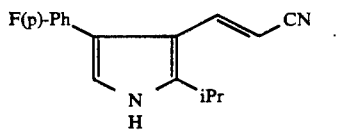

To a suspension of 631 mg (15.8 mmol) of 60% NaH in anhydrous THF is added dropwise a solution of 2.62 g (14.8 mmol) of diethyl cyanomethylphosphonate in 15 ml of anhydrous THF under nitrogen atmosphere for 1 hour. The reaction mixture is stirred at the same temperature for 30 minutes, a solution of 3.67 g (9.85 mmol) of the compound 4 in 40 ml of anhydrous THF is added thereto for 45 minutes. The mixture is warmed up to room temperature and mixed with ice-water. The solution is extracted with ether, washed with water, and concentrated under reduced pressure to give 4.71 g of oil. To a solution of this oil in a mixture of 30 ml of THF and 100 ml of methanol is added 20 ml of 10% NaOH, and the mixture is stirred at 50° C. for 1 hour. The mixture is neutralized with 10% HCl, extracted with methylene, chlorine, washed with water, and concentrated under reduced pressure. The obtained 2.84 g of crude crystals are purified by column chromatography with silica gel, eluting with methylene chloride to give 2.11 g (Yield: 84.2%) of the crystalline compound 5.

NMR (CDCl$_3$) δ: 1.32 (d, 6H, J=7 Hz); 3.24 (septet, 1 Hz, J=7 Hz); 5.09, 7.36 (ABq, 2H, J=16,6 Hz); 6.62 (d, 1H, J=2.4 Hz); 7.03–7.13 (m, 2H); 7.23–7.33 (m, 2H); 8.24 (br, 1H).

(6)
β-[4-(4-Fluorophenyl)-2-isopropyl-1-(2-thiophenesulfonyl)-pyrrol-3-yl]-(E)-acrylonitrile 6

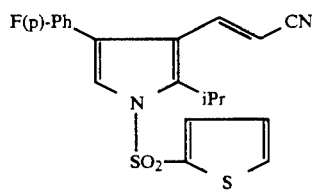

To a suspension of 48 mg (1.2 mmol) of 60% NaH in 4 ml of anhydrous DMF is added dropwise a solution of 256 mg (1 mmol) of the compound 5 in 3 ml of anhydrous DMF under nitrogen atmosphere for 5 minutes. The reaction mixture is stirred at the same temperature for 30 minutes, and a solution of 201 mg (1.1 mmol) of 2-thiophenonesulfonylchloride in 3 ml of anhydrous DMF is added dropwise thereto for 5 minutes. The reaction mixture is warmed up to the room temperature and stirred for 3 hours. To the mixture is added ice-water, and the solution is extracted with ether, washed with water, and concentrated under reduced pressure to give 413 mg (Yield: 103%) of the compound 6 as crude crystals.

NMR (CDCl$_3$) δ: 1.26 (d, 6H, J=7 Hz); 3.86 (septet, 1H, J=7 Hz); 4.93, 7.47 (ABq, 2H, J=16,6 Hz); 7.05–7.30 (m, 6H ); 7.34–7.78 (m, 2H).

(7)
3-[4-(4-fluorophenyl)-2-isopropyl-1-(2-thiophenesulfonylpyrrol-3-yl]-(E)-propenal (II$^{-1}$)

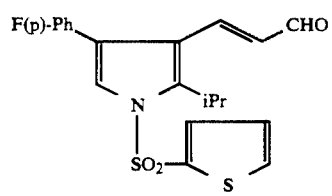

To a solution of 408 mg (1.02 mmol) of the compound 6 in 15 ml of anhydrous THF is added dropwise 3.6 ml of 1M-DIBAL in toluene under nitrogen atmosphere for 5 minutes, and the reaction mixture is stirred at room temperature for 2 hours. To the mixture are added ice and saturated NaH₂PO₄ in order, and the mixture is extracted with methylene chloride. The insoluble material is filtered off on the celite. The organic layer is concentrated under reduced pressure, and the residue is subjected to column chromatography with silica gel to give 225 mg (Yield: 54.6%) of the compound (II-1).

NMR (CDCl₃) δ: 1.31 (d, 6H, J=7 Hz); 3.92 (septet, 1H, J=7 Hz); 5.83 (dd, 1H, J=16, 8 Hz); 7.02-7.29 (m, 6H); 7.58 (d, 1H, J=16 Hz); 7.76 (d, 2H, J=4 Hz); 9.44 (d, 1H, J=8 Hz).

(8) Ethyl 7-[4-(4-fluorophenyl)-2-isopropyl-1-(2-thiophenesulfonyl)pyrrol-3-yl]-5-hydroxy-3-oxo-(E)-6-heptenate (III-1)

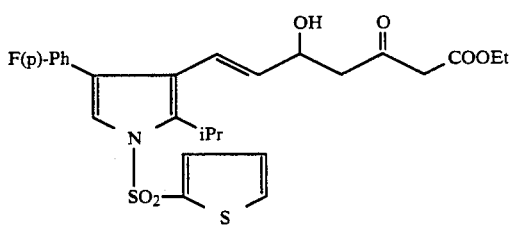

To a suspension of 72 mg (1.80 mmol) of 60% NaH in 5 ml of anhydrous THF is added dropwise a solution of 234 mg (1.80 mmol) of ethyl acetoacetate in 5 ml of anhydrous THF under nitrogen atmosphere under ice-cooling for 5 minutes. The reaction mixture is stirred at the same temperature for 30 minutes, 1.02 ml (1.64 mmol) of 1.6M-nBuLi in n-hexane is added dropwise thereto for 5 minutes. The reaction mixture is stirred further 30 minutes, and a solution of 220 mg (0.545 mmol) of the compound (II-1) in 5 ml of anhydrous THF is added dropwise thereto at −78° C. for 5 minutes. The reaction mixture is stirred further 2 hours and poured into a mixture of acetic acid and ice. The mixture is adjusted to pH 8 with NaHCO₃, and extracted with ether. The organic layer is washed with water and concentrated under reduced pressure to give 0.41 g of oil. It is subjected to column chromatography with silica gel, eluting with methylene chloride/ethyl acetate (20/1) to give 227 mg (Yield: 78.0%) of the compound (III-1).

NMR (CDCl₃) δ: 1.22 (d, 6H, J=7 Hz); 1.26 (t, 3H, J=7 Hz); 2.59-2.67 (m, 2H); 3.42 (s, 2H); 3.74 (septet, 1H, J=7 Hz); 4.19 (q, 2H, J=7 Hz); 4.57 (m, 1H); 5.23 (dd, 1H, J=16,6 Hz); 6.62 (dd, 1H, J=16, 1 Hz); 7.00-7.32 (m, 6H); 7.67-7.71(m, 2H).

(9) Ethyl 7-[4-(4-fluorophenyl)-2-isopropyl-1-(2-thiophensulfonyl)-pyrrol-3-yl]-(3R*,5S*)-dihydroxy-(E)-6-heptenate (Ib-1)

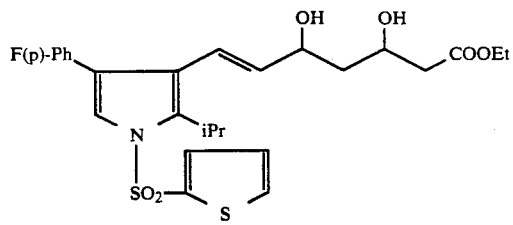

To a solution of 220 mg (0.545 mmol) of the compound (III-1) in 6.3 ml of anhydrous THF and 1.6 ml of anhydrous methanol is added dropwise 0.459 ml (0.6 mmol) of 1M-diethylmethoxyborane in THF under nitrogen atmosphere for 5 minutes, and the reaction mixture is stirred at the same temperature for 1 hour. To the mixture is added 18 mg (0.6 mmol) of NaBH₄, and the mixture is stirred for 2 hours. The reaction mixture is mixed with 0.5 ml of acetic acid, adjusted to pH8 with saturated NaHCO₃ and extracted with ether. The organic layer is washed with water and concentrated under reduced pressure. To the obtained residue is added methanol, the solution is concentrated under reduced pressure. This pressure is repeated for 3 times and the obtained residue 210 mg is subjected to column chromatography with silica gel, eluting with methylene chloride/ethyl acetate (20/1) to give 180 mg (Yield: 80.6%) of the compound (Ib-1).

NMR (CDCl₃) δ: 1.20-1.30 (m, 9H); 1.40-1.60 (m, 2H); 2.42-2.45 (m, 2H); 3.13 (d, 1H, J=2 Hz); 3.66 (d, 1H, J=3 Hz); 3.74 (septet, 1H, J=7 Hz); 4.17 (q, 2H, J=7 Hz); 4.36 (m, 1H); 5.23 (dd, 1H, J=16, 6 Hz).

(10) 7-[4-(4-Fluorophenyl)-2-isopropyl-1-(2-thiophenesulfonyl)-pyrrol-3-yl]-3(R*),5(S*)-dihydroxy-(E)-6-heptenoic acid (Ia1)

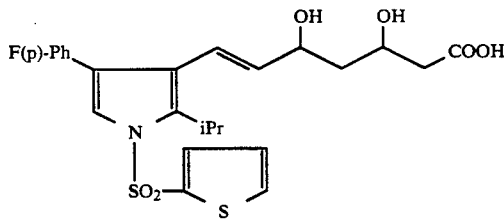

To a solution of 161 mg (0.3 mmol) of the compound (Ib-1) in 5 ml of methanol and 0.5 ml of water is added 0.3 ml (0.6 mmol) of 2N-NaOH, and the mixture is stirred at room temperature for 1 hour and adjusted pH7 with 2N-HCl. The reaction mixture is extracted with methylene chloride, washed with saturated NaCl and concentrated under reduced pressure to give 116 mg (Yield: 76.2%) of the compound (Ia-1).

NMR (CDCl₃-CD₃OD=7:2)δ: 1.21 (d, 6H, J=7 Hz); 1.45 (m, 2H); 2.38-2.40 (m, 2H); 3.73 (septet, 1H, J=7 Hz); 4.11 (m, 1H); 4.28 (m, 1H); 5.25 (dd, 1H, J=16,7 Hz); 6.54 (d, 1H, J=16 Hz); 6.98-7.38 (m, 6H); 7.68-7.76 (m, 2H).

EXAMPLE 2-13

The reactions are performed in the same process as Example 1(1)-(10) to give the compound (Ia) and (Ib). The physical constants are shown in Tables 1, 2, and 3.

TABLE 1

[Reaction scheme: Starting material with F(p)-Ph, COOEt, iPr, N-H pyrrole → Ib intermediate (F(p)-Ph, OH, OH, COOR⁵, iPr, N-SO₂-R⁴) → Ia product (F(p)-Ph, OH, OH, COOH, iPr, N-SO₂-R⁴)]

| Ex. No. | R⁴ | R⁵ | Ib Yield, NMR (CDCl₃) | Ia Yield, NMR (CDCl₃/CD₃OD = 7/2) |
|---|---|---|---|---|
| 2 | (4-methylphenyl) | Et | Ib-2 (86.9%) 1.099(d, 6H, J=7Hz); 1.107(d, 3H, J=7Hz); 1.26(t, 3H, J=7Hz); 1.36-1.63(m, 2H); 2.41-2.45(m, 2H); 3.07(d, 1H, J=2Hz); 3.55(septet, 1H, J=7Hz); 3.63(d, 1H, J=3Hz); 4.10-4.22(m, 3H); 4.36(m, 1H); 5.26(dd, 1H, J=16, 6Hz); 5.56(dd, 1H, J=16, 1Hz); 6.98-7.07(m, 2H); 7.26-7.34(m, 3H); 7.50-7.68(m, 3H); 7.78-7.83(m, 2H) | Ia-2 (90.6%) 1.099(d, 6H, J=7Hz); 1.20-1.65(m, 2H); 2.29(m, 2H); 3.53(septet, 1H, J=7Hz); 4.00(m, 1H); 4.25(m, 1H); 5.24(dd, 1H, J=16, 6Hz); 6.50(d, 1H, J=16Hz); 6.98-7.06(m, 2H); 7.28-7.39(m, 2H); 7.53~7.83(m, 5H) |
| 3 | (4-bromophenyl) | Et | Ib-3 (79.5%) 1.15(d, 6H, J=7Hz); 1.27(t, 3H, J=7Hz); 1.39-1.63(m, 2H); 2.42-2.45(m, 2H); 3.12(d, 1H, J=2Hz); 3.54(septet, 1H, J=7Hz); 3.63(d, 1H, J=2Hz); 4.10-4.22(m, 3H); 4.36(m, 1H); 5.25(dd, 1H, J=16, 6Hz); 6.56(dd, 1H, J=16, 1Hz); 6.98-7.07(m, 2H); 7.24-7.33(m, 3H); 7.67(m, 4H) | Ia-3 (83.6%) 1.13(d, 6H, J=7Hz); 1.25-1.60(m, 2H); 2.32(m, 2H); 3.53(septet, 1H, J=7Hz); 4.09(m, 1H); 4.26(m, 1H); 5.25(dd, 1H, J=16, 6Hz); 6.51(d, 1H, J=16Hz); 6.98-7.06(m, 2H); 7.25-7.33(m, 2H); 7.36(s, 1H); 7.70(m, 4H) |
| 4 | (thiophen-2-yl) | Me | Ib-4 (92.7%) 1.24(d, 6H, J=7Hz); 1.30-1.62(m, 2H); 2.42-2.46(m, 2H); 3.70(s, 3H); 3.80(septet, 1H, J=7Hz); 4.16(m, 1H); 4.36(m, 1H); 5.26(dd, 1H, J=16, 6Hz); 6.57(dd, 1H, J=16, 1Hz); 6.98-7.07(m, 2H); 7.23-7.33(m, 3H); 7.48(m, 2H); 7.83-7.96(m, 3H) | Ia-4 (95.2%) (CDCl₃) 1.23(d, 6H, J=7Hz); 1.30-1.66(m, 2H); 2.49(d, 2H, J=6Hz); 3.80(septet, 1H, J=7Hz); 4.19(m, 1H); 4.37(m, 1H); 5.26(dd, 1H, J=16, 6Hz); 6.57(dd, 1H, J=16, 1Hz); 6.98-7.07(m, 2H); 7.23-7.32(m, 3H); 7.50(m, 2H); 7.83-7.96(m, 3H) |
| 5 | (quinolin-8-yl) | Et | Ib-5 (85.2%) 1.052(d, 3H, J=7Hz); 1.076(d, 3H, J=7Hz); 1.26(t, 3H, J=7Hz); 1.38-1.63(m, 2H); 2.42-2.44(m, 2H); 3.10(brs, 1H); 3.60(septet, brs, 2H); 4.11-4.21(q⁺brs, 3H); 4.35(m, 1H); 5.25(dd, 1H, J=16, 6Hz); 5.56(d, 1H, J=16, 1Hz); 6.98-7.07(m, 2H)7.27-7.36(m, 3H); 7.51-7.70(m, 3H); 8.10-8.27(m, 2H); 9.02(m, 1H) | Ia-5 63.5%) 1.034(d, 3H, J=7Hz); 1.058(d, 3H, J=7Hz); 1.20-1.65(m, 2H); 2.33-2.36(m, 2H); 3.58(septet, 1H, J=7Hz); 4.08(m, 1H); 4.25(dd, 1H, J=16, 6Hz); 5.24(dd, 1H, J=16, 6Hz); 6.52(d, 1H, J=16Hz); 6.98-7.07(m, 2H); 7.29-7.40(m, 2H); 7.54-7.73(m, 3H); 8.12-8.33(m, 3H); 9.02(m, 1H) |
| 6 | (6-methylnaphthalen-2-yl) | Et | Ib-6 (84.7%) 1.082(d, 3H, J=7Hz); 1.088(d, 3H, J=7Hz); 1.36-1.62(m, 2H); 2.40-2.43(m, 2H); 3.10(brs, 1H); 3.67(septet, brs, 2H); 4.09-4.20(q⁺, brs, 3H); 4.34(m, 1H); 5.25(dd, 1H, J=16, 6Hz); 6.54(dd, J=16, 1Hz); 7.26-7.34(m, 3H); 7.63-7.72(m, 2H); 7.89-8.01(m, 3H); 8.46(d, 1H, J=1Hz) | Ia-6 (67.8%) 1.09(d, 6H, J=7Hz); 1.40-1.65(m, H); 2.41(d, 2H, J=6Hz); 3.66(septet, 1H, J=7Hz); 4.12(m, 1H); 4.28(m, 1H); 5.26(dd, 1H, J=16, 6Hz); 6.53(d, 1H, J=16Hz); 7.01-7.11(m, 2H); 7.30-7.38(m, 3H); 7.66-7.76(m, 3H); 7.93-8.05(m, 3H); 8.48(d, 1H, J=2Hz) |

TABLE 1-continued

[Reaction scheme: structure (Ib) with COOR⁵, OH, OH groups and F(p)-Ph, iPr, N-SO₂-R⁴ pyridine → structure (Ia) with COOH, OH, OH groups and F(p)-Ph, iPr, N-SO₂-R⁴ pyridine]

| Ex. No. | R⁴ | R⁵ | Ib Yield, NMR (CDCl₃) | Ia Yield, NMR (CDCl₃/CD₃OD = 7/2) |
|---|---|---|---|---|
| 7 | naphthyl | Et | Ib-7 (82.1%) 0.996(d, 3H, J=7Hz); 1.007(t, 3H, J=7Hz); 1.26(t, 3H, J=7Hz); 1.38-1.63(m, 2H); 2.41-2.44(m, 2H); 3.11(brs, 1H); 3.46 (septet, 1H, J=7Hz); 3.65(d, 1H, J=2Hz); 4.11-4.22(q⁺ brs, 3H); 4.34(m, 1H); 5.25(dd, 1H, J=16, 6Hz); 6.54(d, 1H, J=16Hz); 7.00-7.09(m, 3H); 7.27-7.36(m, 2H); 7.45(s, 1H); 7.53-7.70(m, 3H); 7.94-7.99(m, 2H); 8.12-8.16(m, 1H); 8.52-8.58(m, 1H) | Ia-7 (79.0%) 0.98(d, 6H, J=7Hz); 1.30-1.60(m, 2H); 2.35(m, 2H); 3.45(septet, 1H, J=7Hz); 4.10(m, 1H); 4.25(m, 1H); 5.24(dd, 1H, J=16, 6Hz); 6.50(d, 1H, J=16Hz); 7.00-7.09(m, 2H); 7.29-7.38(m, 3H); 7.46(s, 1H); 7.56-7.72(m, 3H); 7.96-8.02(m, 2H); 8.17(d, 1H, J=8Hz); 8.54(d, 1H, J=8Hz) |
| 8 | mesityl (2,4,6-Me₃-Ph) | Et | Ib-8 (73.1%) 0.992(d, 3H, J=7Hz); 1.004(d, 3H, J=7Hz); 1.40-1.63(m, 2H); 2.32(s, 3H); 2.42-2.46(m, 2H); 2.48 (s, 6H); 3.04(septet, 1H, J=7Hz); 3.64(d, 1H, J=2Hz); 4.11-4.19(q⁺ brs, 3H); 4.35(brs, 1H); 5.26(dd, 1H, J=16, 6Hz); 6.56(dd, 1H, J=16, 1Hz); 6.96-7.06(m, 4H); 7.26-7.33(m, 3H) | Ia-8 (100%) 1.01(d, 6H, J=7Hz); 1.40-1.65(m, 2H); 2.34(s, 3H); 2.43(s, 2H); 2.49(s, 6H); 3.08(septet, 1H, J=7Hz); 4.12(m, 1H); 4.28(m, 1H); 5.27(dd, 1H, J=16, 6Hz); 6.55(d, 1H, J=16Hz); 7.00-7.08(m, 4H); 7.26-7.44(m, 3H) |
| 9 | 2-biphenyl | Et | Ib-9 (82.3%) 0.983(d, 3H, J=7Hz); 1.27(t, 3H, J=7Hz); 1.35-1.63(m, 2H); 2.42-2.47(m, 2H); 3.05-3.27(m, 2H); 3.67(d, 1H, J=2Hz); 4.12-4.22(q⁺ brs, 3H); 4.36(m, 1H); 5.20(dd, 1H, J=16, 6Hz); 6.18(s, 1H); 6.54(d, 1H, J=16Hz); 6.92-7.32(m, 10H); 7.54-7.70(m, 2H); 8.17(m, 1H) | Ia-9 (94.7%) 1.01(d, 6H, J=7Hz); 1.40-1.70(m, 2H); 2.44(d, 2H, J=6Hz); 3.16(septet, 1H, J=7Hz); 4.13(m, 1H); 4.33 (m, 1H); 5.22(dd, 1H, J=16, 6Hz); 6.52 (d, 1H, J=16Hz); 6.94-7.44(m, 10H); 7.66(m, 2H); 8.15-8.20(m, 1H) |
| 10 | | Me | Ib-10 (79.3%) 1.28(t, 3H, J=7Hz); 1.41(d, 6H, J=7Hz); 1.48-1.75(m, 2H); 4.18 4.55(m, 2H); 3.22(s, 3H); 3.67(septet, 1H, J=7Hz); 4.18 (q, 2H, J=7Hz); 4.29(brs, 1H); 4.41(brs, 1H); 5.31(dd, 1H, J=16, 6Hz); 6.64(dd, 1H, J=16, 1Hz); 7.02(m, 2H); 7.28(m, 2H) | Ia-10 (87.8%) 1.41(d, 2H, J=7Hz); 1.50-1.70(m, 2H); 2.53(d, 2H, J=6Hz); 3.22(s, 2H); 3.67(septet, 1H, J=7Hz); 4.25 5(m, 1H); 4.44(m, 1H); 5.31(dd, 1H, J=16, 6Hz); 6.64 (d, 1H, J=16Hz); 7.05(m, 2H); 7.28(m, 2H) |

TABLE 2

| Ex. No. | R⁴ | R⁵ | (I) (g, %, °C). | Aanl Calcd. (%) for: | |
|---|---|---|---|---|---|
| 11 | 4-Br-C₆H₄ | Me | Ib-11 0.35 g (94.3%) 64~65° C. | Ia-11 0.27 g (93.8%) 104° C.~ | Ib-11 ($C_{27}H_{29}NSBrFO_6$) : C, 54.55; H, 4.92; N, 2.36; S, 5.39 Br, 13.44; F, 3.20 Found: C, 54.98; H, 5.16; N, 2.62; S, 5.48 Br, 13.73; F, 3.84 | Ia-11 ($C_{26}H_{27}NSBrFO_6\cdot0.25Et_2O$) : C, 54.14; H, 4.96; N, 2.34; S, 5.35 F, 3.17 Found: C, 54.40; H, 5.02; N, 2.39; S, 5.41 F, 2.87 |
| 12 | 2-thienyl | Me | Ib-12 0.51 g (94.1%) 45° C.~ | Ia-12 0.28 g (92.7%) | Ib-12 ($C_{26}H_{28}NS_2FO_6$) : C, 57.57; H, 5.41; N, 2.69; S, 12.29 F, 3.64 Found: C, 57.07; H, 5.56; N, 2.68; S, 12.23 F, 3.86 | Ia-12 ($C_{24}H_{26}NS_2FO_6$) : C, 56.79; H, 5.16; N, 2.76; S, 12.63 F, 3.74 Found: C, 56.56; H, 5.33; N, 2.86; S, 12.73 F, 3.73 |

TABLE 3

| Ex. No. | (I) (g, %, °C.) | Anal Calcd. (%) for: | |
|---|---|---|---|
| 13 | Ib-13 0.34 g (89.5%) 101~103° C. | Ia-13 0.17 g (83.3%) | Ib-13 ($C_{28}H_{32}NSFO_6$) : C, 63.50; H, 6.09; N, 2.64; S, 6.05 F, 3.59 Found: C, 63.37; H, 6.02; N, 2.60; S, 6.14 F, 3.89 | Ia-13 ($C_{27}H_{30}NSFO_6$) : C, 62.90; H, 5.87; N, 2.72; S, 6.22 F, 3.68 Found: C, 62.53; H, 6.07; N, 2.99; S, 6.08 F, 3.48 |

EXAMPLE 14

(1)

4-(4-Fluorophenyl)-3-formyl-2-isopropyl-5-methyl-1-methylsulfonylpyrrole 7

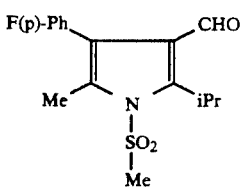

As a starting material, a mixture of 6.33 g (40 mmol) of ethyl isobutyrylacetate, 12.22 g (60 mmol) of 2-amino-4'-fluoropropiophenonehydrochloride, 1 ml of acetic acid, 5.58 g of sodium acetate, and 0.7 ml of water is reacted in the same process as Example 1 (1) to (4) to give 1.42 g (Yield: 79.8%) of the compound 7. mp. 126°-127° C.

Anal: Calcd. (%) for $C_{16}H_{18}NSFO_3$: C, 59.43; H, 5.61; N, 4.33; S, 9.91; F, 5.87. Found: C, 59.43; H, 5.60; N, 4.32 S, 10.13; F, 5.58.

(2)

β-[4-(4-Fluorophenyl)-2-isopropyl-5-methyl-1-methyl-sulfonylpyrrol-3-yl]-(E)-acrylonitrile 8

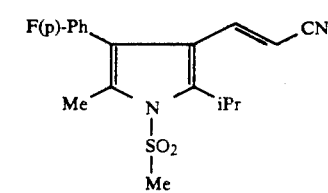

To a suspension of 0.77 g of 60% NaH in 40 ml of THF is added dropwise a solution of 1.70 g (9.6 mmol) of diethyl cyanomethylphosphonate in 10 ml of THF under ice-cooling, and the mixture is stirred for 45 minutes. To the mixture is added dropwise a solution of 2.07 g (6.4 mmol) of the compound 7 in 30 ml of THF, and the mixture is stirred for 2 hours and mixed with ice-water. The solution is extracted with ether and washed with water. The ether layer is dried over Na₂SO₄ and evaporated under reduced pressure. The residue is subjected to column chromatography with silica gel, eluting with hexane-ether (¼) to give 0.58 g (Yield: 26.1%) of the compound 8. Recrystallization from ether gives the crystals melting at 137°–139° C.

Anal Calcd. (%) for $C_{18}H_{19}N_2SFO_2$: C, 62.41: H, 5.53; N, 8.09; S, 9.25; F, 5.48. Found: C, 62.55; H, 5.56; N, 8.07; S, 9.39; F, 5.78.

(3) Methyl 7-[4-(4-fluorophenyl)-2-isopropyl-5-methyl-1-methyl-sulfonylpyrrol-3-yl]-(3R*,5S*)-dihydroxy-(E)-6-heptenate (Ib-14)

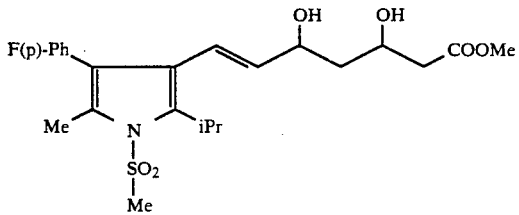

The compound 8 is reacted in the same process as Example 1 (7) to (9) to give 0.25 g (Yield: 99.6%) of the compound (Ib-14) as syrup.

NMR (CDCl₃) δ: 1.39 (d, J=7 Hz, 6H); 2.24 (s, 3H); 2.44 (d, J=7 Hz, 2H); 3.18 (s, 3H); 3.72 (s, 3H); 3.84 (m, 1H); 4.31 (m, 1H); 5.01 (dd, J=16,6 Hz, 1H); 6.57 (dd, 16,1 Hz, 1H); 7.10 (m, 4H).

(4) 7-[4-(4-Fluorophenyl)-2-isopropyl-5-methyl-1-methyl-sulfonylpyrrol-3-yl]-(3R*,5S*)-dihydroxy-(E)-6-heptenoic acid (Ia-14)

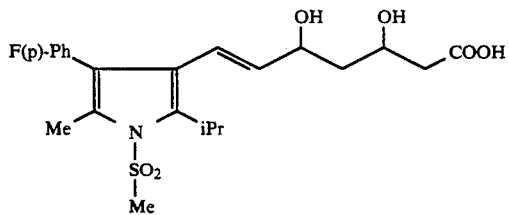

The compound (Ib-14) 0.12 g (0.26 mmol) is reacted in the same manner as Example 1 (10) to give 0.1 g (Yield: 84.7%) of the compound (Ia-14) as powder.

NMR (CDCl₃) δ: 1.37 (d, J=7 Hz, 6H); ;2.24 (s, 3H); 2.50 (d, J=6 Hz, 2H); 3.18 (s, 3H); 3.84 (m, 1H); 4.17 (m, 1H); 4.33 (m, 1H); 5.10 (dd, J=16,6 Hz, 1H); 6.57 (dd, J=16,1 Hz, 1H); 7.12 (m, 4H).

Anal Calcd. (%) for $C_{22}H_{28}NSFO_6 \cdot 0.25H_2O$: C, 57.69; H, 6.27; N, 3.06; S, 7.00. Found: C, 57.57; H, 6.30; N, 3.04; S, 6.71.

Example 15

(1) Ethyl 4-isopropyl-2-(4-fluorophenyl)pyrrole-3-carboxylate 9

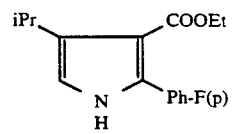

A mixture of 9.91 g (72.0 mmol) of 3-methyl-2-oxobutylamine-hydrochloride, 12.6 g (59.9 ) of ethyl 4-fluorobenzoate, 8.37 g of sodium acetate, 22.8 ml of acetic acid, and 15.6 ml of water is reacted in the same manner as Example 1 (1) to give 9.06 g (Yield: 54.9%) of the compound 9. mp. 108°–109° C. Anal Calcd. (%) for $C_{16}H_{18}NFO_2$: C, 69.80; H, 6.59; N, 5.09; F, 6.90. Found: C, 69.84; H, 6.61; n, 5.18; F, 6.72.

(2) 2-(4-Fluorophenyl)-3-formyl-4-isopropyl-1-(8-quinolylsulfonyl)-pyrrole 10

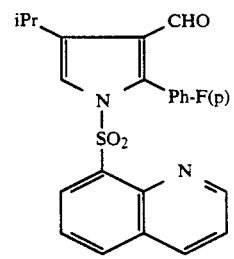

The compound 9 7.02 g is reacted with quinoline-8-sulfonylchloride and treated in the same process as Example 1 (2) to (4) to give 5.63 g (Yield: 78.1%) of the compound 10. mp. 157°–158° C.

Anal Calcd. (%) for $C_{23}H_{19}N_2SFO_3$: C, 65.39; H, 4.53; N, 6.63; S, 7.59; F, 4.50. Found C, 65.50; H, 4.64; N, 6.67: S, 7.57; F, 4.24.

(3) Methyl 7-[2-(4-fluorophenyl)-4-isopropyl-1-(8-quinolinesulfonyl)pyrrol-3-yl]-(3R*,5S*)-dihydroxy-(E)-6-hepenate (Ib-15)

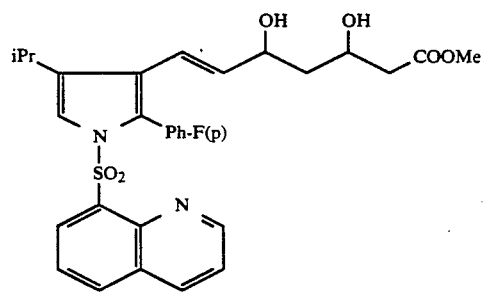

The compound 10 5.36 g is reacted in the same process as Example 14 (1) to (3) to give 0.19 g (Yield: 84.8%) of the compound (Ib-15).

Anal Calcd. (%) for $C_{30}H_{31}N_2SFO_5 \cdot 0.5H_2O$: C, 62.60; H, 5.60; N, 4.87; S, 5.57; F, 3.30. Found: C, 62.60; H, 5.55; N, 4.78; S, 5.47; F, 2.76.

(4)
7-[2-(4-Fluorophenyl)-4-isopropyl-1-(8-quinolinesulfonyl)-pyrrol-3-yl]-(3R*,5S*)-dihydroxy-(E)-6-heptenoic acid (Ia-15)

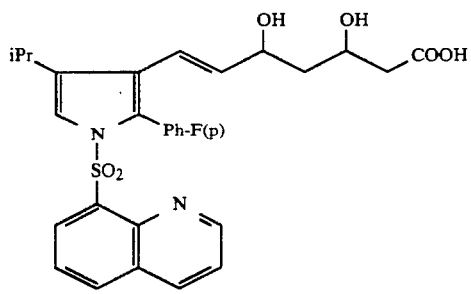

The compound (Ib-15) 0.14 g is reacted in the same manner as Example 14 (4) to give 0.13 g (Yield: 94.9%) of the compound (Ia-15).

Anal Calcd. (%) for $C_{29}H_{29}N_2SFO_6 \cdot 0.6H_2O$: C, 61.82; H, 5.40; N, 4.97; S, 5.69; F, 3.37. Found: C, 61.64; H, 5.40; N, 4.90; S, 5.76; F, 3.56.

EXAMPLE 16

(1)
2-(4-Fluorophenyl)-3-formyl-4-isopropyl-1-phenylsulfonylpyrrole 11

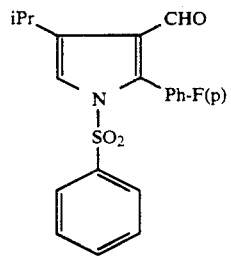

The compound 11 1.03 g (Yield: 94.3%) is prepared by the reaction of 0.769 g of methyl 4-isopropyl-2-(4-fluorophenylpyrrole)-3-carboxylate with benzenesulfonyl chloride.

NMR (CDCl$_3$) δ: 1.25 (d, J=7,6 Hz); 3.37 (septet, J=7 Hz, 1H); 7.08 (m, 4H); 7.27–7.62 (m, 6H); 9.36 (s, 1H).

(2) Ethyl 7-[2-(4-fluorophenyl)-4-isopropyl-1-phenylsulfonylpyrrol-3-yl]-(3R*,5S*)-dihydroxy-(E)-6-heptenate (Ib-16)

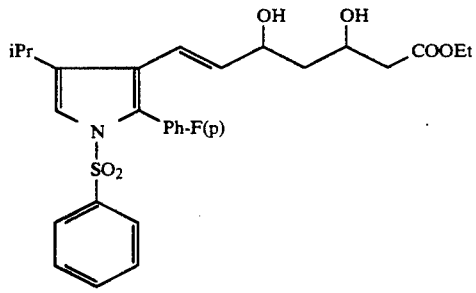

The compound (Ib-16) 0.185 g (Yield: 76.8%) is prepared by the reaction of the compound 11 in the same manner as Example 15 (3).

(3)
7-(2-(4-Fluorophenyl)-4-isopropyl-1-phenylsulfonyl-pyrrol-3-yl]-(3R*,5S*)-dihydroxy-(E)-6-heptenoic acid (Ia-16)

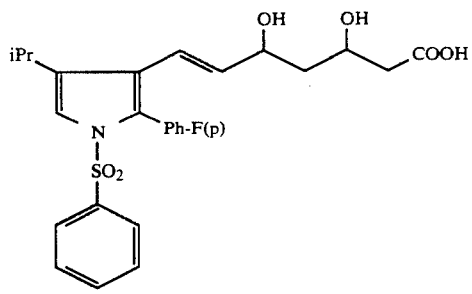

The compound (Ib-16) is reacted in the same manner as Example 15 (4) to give 0.134 g (Yield: 78.6%) of the compound (Ia-16).

EXAMPLE 17

(1)
4,5-Di-(4-fluorophenyl)-3-formyl-2isopropyl-1-methylsulfonylpyrrol 12

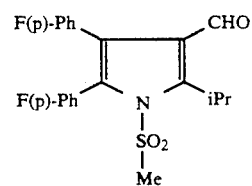

A mixture of 0.53 g (3.4 mmol) of ethyl isobutyrylacetate, 1.52 g (5.4 mmol) of 2-amino-2-(4-fluorophenyl)-4'-fluoroacetophenone, 1.28 ml of acetic acid, 0.46 g of sodium acetate, and 0.88 ml of water is reacted in the same procedure as Example 1 (1) to (4) to give 1.69 g (Yield: 89.4%) of the compound 12. mp. 213°–214° C.

Anal Calcd. (%) for $C_{21}H_{19}NSF_2O_3$: C, 62.52; H, 4.75; N, 3.47; S, 7.95; F, 9.42. Found: C, 62.65; H, 4.91; N, 3.47; S, 7.87; F, 9.20.

(2)
β-[4,5-Di-(4-fluorophenyl)-2-isopropyl-1-methylsulfonylpyrrol-3-yl]-(E)-acrylonitrile 13

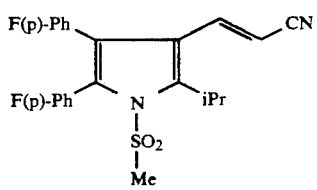

The compound 12 1.68 g (4.2 mmol) is reacted in the same manner as Example 14 (2 to give 0.59 g (Yield: 47.2% of the compound 13. mp. 205°–206° C.

Anal Calcd. (%) for $C_{23}H_{20}N_2SF_2O_2$: C, 64.77; H, 4.73; N, 6.57; F, 8.91; S, 7.52. Found: C, 64.92; H, 4.84; N, 6.59; F, 8.71; S, 7.73.

(3) Methyl 7-[4,5-Di-(4-fluorophenyl)-2-isopropyl-1-methylsulfonylpyrrol-3-yl]-(3R*,5S*)-dihydroxy-(E)-6-heptenate (Ib-17)

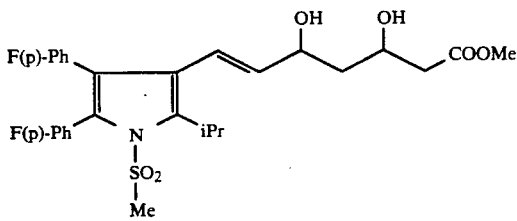

The compound 13 is reacted in the same procedure as Example 1 (7) to (9) to give 0.18 g (yield: 81.8%) of the compound (Ib-17). mp. 127°–128° C.

Anal Calcd. (%) for $C_{28}H_{31}NSF_2O_6 \cdot 0.2H_2O$: C, 61.01; H, 5.74; N, 2.54; S, 5.82; F, 6.89; Found: C, 60.88; H, 5.67; N, 2.58; S, 6.05; F, 6.83.

(4) 7-υ4,5-Di-(4-fluorophenyl)-2-isopropyl-1-(methylsulfonyl)-pyrrol-3-yl]-(3R*,5S*)-dihydroxy-(E)-6-heptenoic acid (Ia-17)

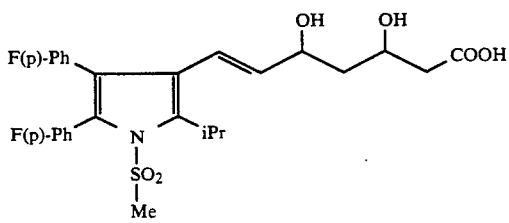

The compound (Ib-17) 0.14 g (0.25 mmol) is reacted in the same manner as Example 1 (10) to give 0.12 g (Yield: 88.2%) of the compound (Ia-17). mp. 157°–159° C. (dec.)

Anal Calcd. (%) for $C_{27}H_{29}NSF_2O_6$: C, 60.78; H, 5.48; N, 2.63; S, 6.01; F, 7.12. Found: C, 60.48; H, 5.58; N, 2.69; S, 6.20; F, 7.41.

EXAMPLE 18

(1) Methyl-7-[4-(4-fluorophenyl)-2-isopropyl-5-methyl-1-(methylsulfonyl)pyrrol-3-yl]-(3R*,5R*)-dihydroxyheptanate (Ib'-14)

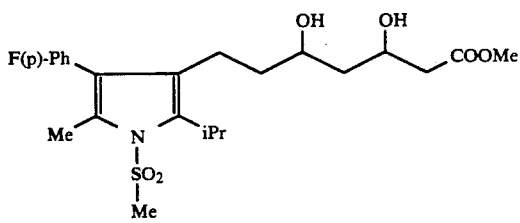

A suspension of 0.17 g of the compound (Ib-14), 10 ml of methanol, and 40 mg of 10% Pd-C is shaken under atmospheric pressure at room temperature under hydrogen atmosphere for 6 hours. After Pd-C is filtered off, the residue is subjected to column chromatography with silica gel, eluting with methylene chloride/ethyl acetate (3/1) to give 0.15 g (Yield: 88.2%) of the compound (Ib'-14) as oil.

NMR (CDCl$_3$) δ: 1.26 (m, 2H); 1.39 (d, J=7.6 Hz, 6H); 2.22 (s, 3H); 2.40 (d, J=5.6 Hz, 2H) 2.59 (m, 2H); 3.14 (s, 3H), 3.64 (m, 1H); 3.71 (s, 3H); 3.78 (m, 1H); 4.11 (m, 1H); 7.13 (m, 4H)

(2) 7-[4-(4-Fluorophenyl)-2-isopropyl-5-methyl-1-(methylsulfonyl)-pyrrol-3-yl]-(3R*,5R*)-dihydroxy-heptanoic acid (Ia'-14)

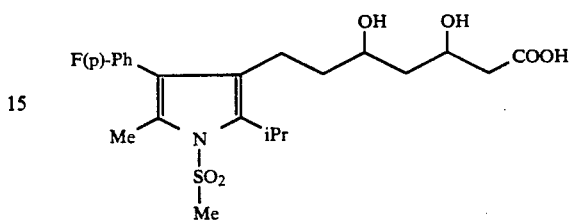

The compound (Ib'-14) 0.16 g is reacted in the same manner as Example 1 (10) to give 0.13 g (yield: 83.9%) of the compound (Ia'-14) as powder.

NMR (CDCl$_3$) δ: 1.28 (m, 2H); 1.38 (d, J=7.4 Hz, 6H); 2.22 (s, 3H); 2.45 (d, J=6.6 Hz, 2H) 2.55 (m, 2H); 3.15 (s, 3H); 3.69 (m, 1H); 3.79 (m, 1H); 4.12 (m, 1H); 7.14 (m, 4H).

EXAMPLE 19

(E)-6(S*)-[2-[1-Phenylsulfonyl-2-(4'-fluorophenyl)-4-isopropyl-1H-pyrrol-3-yl]ethenyl]-4(R*)-hydroxy-3,4,5,6-tetrahydro-2H-pyran-2-one (Ic-1)

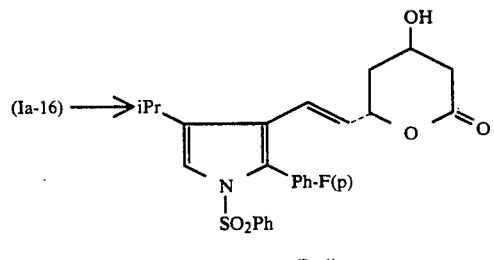

The compound (Ia-16) obtained in Example 16 (3) is left at room temperature for 80 days and purified by column chromatography with silica gel, eluting with methylene chloride/methanol (10/1) to give resinous lactone (Ic-1). Yield: 53.7%

NMR (CDCl$_3$) δ: 1.24 (d, J=7 Hz, 3H); 1.26 (d, J=7 Hz, 3H); 1.55–1.92 (m, 2H); 2.60 (m, 2H); 4.27 (brs, 1H); 5.01 (m, 1H); 5.54 (dd, J=16,7 Hz, 1H); 6.14 (d, J=16 Hz, 1H); 6.98 (m, 5H); 7.24–7.60 (m, 8H) IR (CHCl$_3$) υ cm$^{-1}$: 1725, 1370, 1170.

EXAMPLE 20

Sodium 7-[4-(4-fluorophenyl)-2-isopropyl-5-methyl-1-methylsulfonylpyrrol-3-yl]-(3R*,5S*)-dihydroxy-(E)-6-heptenate (Id-1)

(Ib-14) 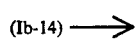

-continued

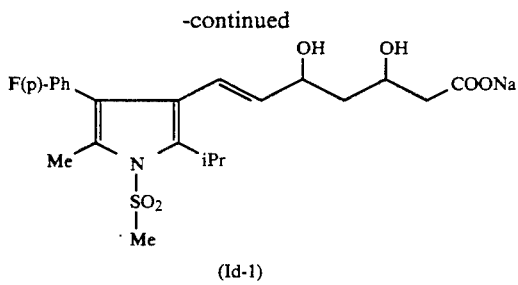

(Id-1)

To a solution of 0.185 g (0.396 mmol) of the compound (Ib-14) obtained in Example 14 (3) in 4 ml of methanol is added a solution of 3.96 ml (0.396 mmol) of 0.1N-NaOH, and the mixture is stirred at room temperature for 1 hour and concentrated under reduced pressure to remove methanol. To the residue is added 15 ml of water, and the solution is freeze-dried to give 0.184 g (Yield: 95.3%) of the compound (Id-1) as powder. mp. 167° C.

Anal Calcd. (%) for $C_{22}H_{27}NSFNaO_6 \cdot 0.75H_2O$: C, 54.04; H, 5.87; N, 2.86; S, 6.56; Na, 4.70. Found: C, 53.81; H, 5.81; N, 3.04; S, 6.93; Na, 4.84.

EXAMPLE 21

(1) Methyl 7-[4-(4-fluorophenyl)-2isopropyl-5-methyl-1-ethylsulfonylpyrrol-3-yl]-5-hydroxy-3-oxo-(E)-6-heptenate (III-2)

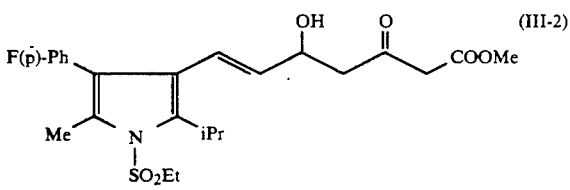

β-[4-(4Fluorophenyl)-2-isopropyl-5-methylpyrrol-3yl]-(E)-acrylonitrile 1.34 g (5.0 mmol) is reacted with 0.71 g (5.5 mmol) of ethanesulfonyl chloride and treated in the same manner as in Example 1 (6) to (7) to give 0.75 g (Yield: 63.6%) of 3-[4-(4-fluorophenyl)-2-isopropyl-5-methyl-1-ethylsulfonylpyrrol-3-yl-(E)-propenal (II-2). To a suspension of 0.26 g (6.5 mmol) of 60% NaH in 6 ml of anhydrous THF is added dropwise a solution of 0.70 g (6.0 mmol) of methyl acetoacetate in 6 ml of anhydrous THF under nitrogen atmosphere for 10 minutes, and 3.75 ml (6.0 mmol) of 1.6M n-BuLi in n-hexane is added dropwise for 5 minutes thereto. The solution is stirred for further 30 minutes, and a solution of the compound (II-2) in 15 ml of anhydrous THF is added dropwise thereto. The mixture is treated in the same manner as Example 1 (8) to give 0.44 g (Yield: 45.7%) of the compound (III-2) as syrup.

NMR (CDCl$_3$) δ: 1.37 (dd, 3H, J=5 Hz); 1.38 (d, 3H, J=5 Hz); 2.23 (s, 3H); 2.51 (d, 2H, J=5.6 Hz); 3.43 (s, 2H); 3.82 (m, 1H); 4.46 (s, 2H); 4.95 (dd, 1H, J=6.4, 16 Hz); 6.61 (dd, 1H, J=1.4,16 Hz); 6.96–7.46 (m, 9H).

(2) 7-[4-(4-Fluorophenyl)-2-isopropyl-5-methyl-(1-ethylsulfonyl)pyrrol-3-yl]-(3R*,5S*)-dihydroxy-(E)-6-heptenate (Ia-18)

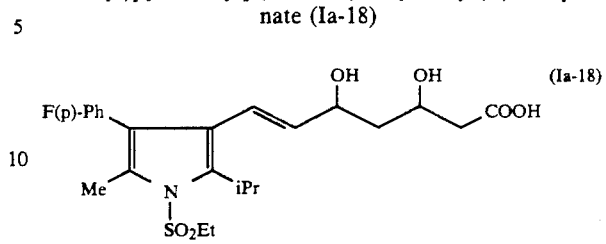

The compound (III-2) 0.43 g (0.9 mmol) is reacted in the same manner as Example 1 (9) to (10) to give 0.21 g (Yield: 98.1%) of the compound (Ia-18) as powder.

NMR (CDCl$_3$) δ: 1.34 (t, 3H, J=7.4 Hz); 1.37 (d, 6H, J=7 Hz); 2.48 (d, 2H, J=6.4 Hz); 3.29 (q, 2H, J=7.4 Hz); 3.82 (m, 1H); 4.14 (brs, 1H); 4.32 (brs, 1H); 4.99 (dd, 1H, J=6.2,16 Hz); 6.58 (dd, 1H, J=0.8,16 Hz); 7.0–7.90 (m, 4H).

EXAMPLE 22

7-[4-(4-Fluorophenyl)-2-isopropyl-5-methyl-(1-benzylsulfonyl)-pyrrol-3-yl]-(3R*,5S*)-dihydroxy-(E)-6-heptenate (Ia-19)

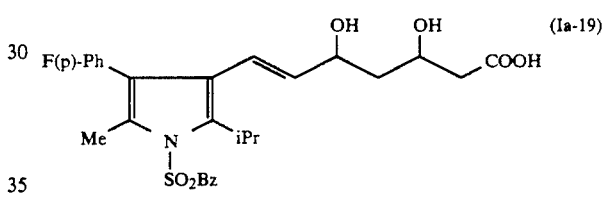

β-[4-(4-Fluorophenyl)-2-isopropyl-5-methylpyrrol-3-yl]-(E)-acrylonitrile 2.03 g (7.6 mmol) is reacted with 1.50 g (7.9 mmol) of α-toluenesulfonyl chloride and treated in the same manner as in Example 21 to give 0.19 g (Yield: 100%) of the compound (Ia-19) as powder.

NMR (CDCl$_3$) δ: 1.36 (dd, 6H, J=1.2,7.2 Hz); 2.49 (d, 2H, J=6 Hz); 3.81 (m, 1H); 4.18 (brs, 1H); 4.33 (brs, 1H); 4.46 (s, 2H); 4.98 (dd, 1H, J=6.5, 16 Hz); 6.57 (dd, 1H, J=1,16 Hz); 6.92–7.45 (m, 9H).

EXAMPLE 23

(1) (+) Ethyl 7-[4-(4-fluorophenyl)-2-isopropyl-5-methyl-(1-methylsulfonyl)pyrrol-3-yl]-(3R,5S)-dihydroxy-(E)-6-heptenate (Ib-17)

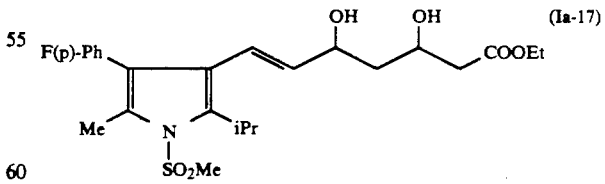

The compound 8 obtained in Example 14 (2) is treated in the same manner as in Example 1 (7) to (9) to give ethyl 7-[4-(4-fluorophenyl)-2-isopropyl-5-methyl-1-methylsulfonylpyrrol-3-yl]-(3R*,5S*)-dihydroxy-(E)-6-heptenate (the racemate of the compound (Ib-17)). The obtained racemate 82.80 g is subjected to racemic resolution on HPLC (High Performance Liquid Chromatography) to give 23.8 g of the compound (Ib-17) (racemic purity 98.6%).

$[\alpha]_D^{25.5} = +13.9 \pm 0.5°$ (C=1.012, in dichloroethane).

(2) (+) Sodium 7-[4-(4-fluorophenyl)-2-isopropyl-5-methyl-(1-methylsulfonyl)pyrrol-3-yl]-(3R,5S)-dihydroxy-(E)-6-heptenate (Ib-2)

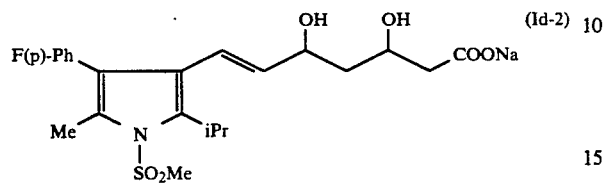

To a solution of 23.22 g (0.0482 mol) of the compound (Ib-17) in 900 ml of ethanol is added 463 ml (0.0468 mol) of 0.1N-NaOH at room temperature, and the mixture is stirred for 2 hours. After removal of ethanol as azeotrope under reduced pressure at 35° C. to give the substance as formed, the substance is mixed with further 300 ml of ether for crystallization to give 22.54 g (Yield: 91.4%) of the compound (Id-2).

Anal Calcd. (%) for $C_{22}H_{27}NO_6SFNa \cdot 2H_2O$: H, 6.11; N, 2.74; S, 6.27; F, 3.71; Na, 4.49. Found: C, 51.79; H, 6.17; N, 2.84; S, 6.12; F, 3.49; Na, 4.63.

NMR (CDCl$_3$) δ: 1.33 (s, 3H); 1.37 (s, 3H); 2.15 (s, 3H); 2.24 (m, 2H); 3.36 (s, 3H); 3.72 (m, 2H); 4.21 (m, 1H); 4.98 (dd, J=16,7 Hz, 1H); 6.62 (d, J=16,1H); 7.14 (m, 4H) $[\alpha]D = +26.3 \pm 0.7°$ (C=1.010, 25.5° C., water).

EVALUATION OF BIOLOGICAL ACTIVITY

Experiment

The HMG-CoA Reductase Inhibitory Effect (1) Preparation of Rat Liver Microsome Sprague-Dawley rats, which were in free access to ordinary diets containing 2% cholestyramine and water for 2 weeks, were used for the preparation of rat liver microsome, which were then purified according to the manner by Kuroda et al., Biochem. Biophys. Act, 486, 70 (1977). The microsomal fraction obtained by centrifugation at 105000×g was washed once with a buffered solution containing 15 mM nicotinamide and 2 mM magnesium chloride (in a 100 mM potassium phosphate buffer, pH 7.4). It was homogenized with a buffer containing nicotinamide and magnesium chloride at the same weight as the liver employed. The thus obtained homogenate was cooled down to and kept at −80° C.

(2) Measurement of the HMG-CoA Reductase Inhibitory Activities

The rat liver microsome (100 μl), which was preserved at −80° C., was fused at 0° C. and diluted with 0.7 ml of a cold potassium phosphate buffer (100 mM, pH 7.4 ). This was mixed with 0.8 ml of 50 mM EDTA (buffered with the aforementioned potassium phosphate buffer) and 0.4 ml of 100 mM dithiothreitol solution (buffered with the aforementioned potassium phosphate buffer), and the mixture was kept at 0° C. The microsome solution, 1.675 ml, was mixed with 670 μl of 25 mM NADPH (buffered with the aforementioned potassium phosphate buffer), and the solution was added to the solution of 0.5 mM [3-$^{14}$C]HMG-CoA (3 mCi/mmol). Potassium phosphate buffer of sodium salt of the test compound 5 μl is added to the mixture of microsome and HMG-CoA 45 μl, and the resulting mixture was incubated at 37° C. for 30 minutes and cooled. After termination of the reaction by addition of 10 μl of 2N-HCl, the mixture was incubated again at 37° C. for 15 minutes and then 30 μl of this mixture was applied to thin-layer chromatography with silica gel of 0.5 mm in thickness (Merck AG, Art 5744). The chromatograms were developed in toluene/acetone (1/1) and the sections, whose Rf value was between 0.45 to 0.6, were scraped. The obtained products were put into a vial containing 8 ml of scintillator to measure specific radioactivity with a scintillation counter. The results are shown in Table 4.

TABLE 4

| Test Compound | HMG—CoA reductase inhibitory activities* |
|---|---|
| Ia-10 | 263 |
| Ia-17 | 293 |
| Ia-18 | 228 |
| Ia-19 | 105 |
| Id-2 | 418 |
| Mevinolin Na | 100 |

*The activities of the present compounds are shown as comparative ones based on the assumption that the activity of Mevinolin (sodium salt) as reference drug is 100.

From the above data, the compounds of the present invention exhibit superior activities to Mevinolin in HMG-CoA reductase inhibition.

What we claim is:

1. A compound represented by the formula:

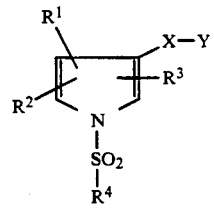

wherein

R$^1$, R$^2$, and R$^3$ each is independently (1) hydrogen, (2) lower alkyl unsubstituted or substituted by 1 to 3 substituents independently selected from the group consisting of halogen, lower alkoxyamino and cyano, or (3) aryl unsubstituted or substituted by 1 to 3 substituents independently selected from the group consisting of lower alkyl, halogen, amino and cyano, R$^4$ is (1) lower alkyl unsubstituted or substituted by 1 to 3 substituents independently selected from the group consisting of halogen, lower alkoxyamino and cyano, (2) aralkyl unsubstituted or substituted by 1 to 3 substituents independently selected from the group consisting of lower alkyl, halogen, amino and cyano, (3) aryl unsubstituted or substituted by 1 to 3 substituents independently selected from the group consisting of lower alkyl, halogen, amino and cyano, or (4) a heteroaryl selected from the group consisting of thienyl, furyl, pyrrolyl, imidazolyl, pyrazolyl, isothiazolyl, pyridyl, pyrimidinyl, pyrazinyl, quinolyl, isoquinolyl, benzothienyl and indolyl, each of which is unsubstituted or substituted by 1 to 3 substituents independently selected from the group consisting of lower alkyl halogen, amino and cyano;

X is vinylene or ethylene; and

Y is

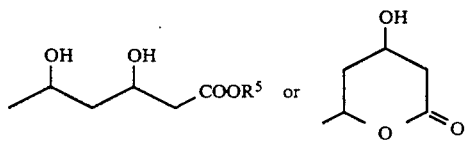

where R⁵ is hydrogen, lower alkyl, aryl, aralkyl, or a cation capable of forming a non-toxic pharmaceutically acceptable salt.

2. The compound claimed in claim 1, wherein X is vinylene.

3. The compound claimed in claim 1, wherein Y is

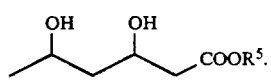

4. The compound claimed in claim 1, wherein X is vinylene and Y id

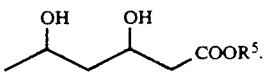

5. The compound claimed in claim 1, wherein said compound takes an optically active form.

6. The compound claimed in claim 1, namely, (+) sodium 7-[4-(4-fluorophenyl)-2-isopropyl-5-methyl-(1-methylsulfonyl)pyrrol-3-yl]-(3R,5S)-dihydroxy-(E)-6-heptenate.

7. A pharmaceutical composition comprising a pharmacologically effective amount of the compound claimed in claim 1 together with a carrier, diluent, and/or excipient.

8. A pharmaceutical composition claimed in claim 7, which is effective as an HMG-CoA reductase inhibitor.

* * * * *